United States Patent
Barritault et al.

[11] Patent Number: 5,852,003
[45] Date of Patent: Dec. 22, 1998

[54] DRUG AND PHARMACEUTICAL COMPOSITION FOR THE TREATMENT OF MUSCLES

[75] Inventors: Denis Barritault, Paris; Jean-Pierre Caruelle, Saint Maur; Pascal Desgranges, Paris; Jean Gautron, Vitry sur Seine; Anne Meddahi, Creteil, all of France

[73] Assignee: Societe Valbiofrance, Creteil Cedex, France

[21] Appl. No.: 714,176

[22] PCT Filed: Mar. 29, 1995

[86] PCT No.: PCT/FR95/00398

§ 371 Date: Jan. 3, 1997

§ 102(e) Date: Jan. 3, 1997

[87] PCT Pub. No.: WO95/26736

PCT Pub. Date: Oct. 12, 1995

[30] Foreign Application Priority Data

Mar. 30, 1994 [FR] France .................................. 94 03803

[51] Int. Cl.⁶ .......................... A61K 31/715; C08B 37/00
[52] U.S. Cl. .......................... 514/54; 536/55.2; 536/103; 536/123.1; 536/124
[58] Field of Search ................................ 514/54; 536/103, 536/55.2, 123.1, 124

[56] References Cited

PUBLICATIONS

J. Biomater. Sci. Polym. Ed., vol. 3, No. 2, issued 1991, Avramoglou et al, pp. 149–154.

*Primary Examiner*—Douglas W. Robinson
*Assistant Examiner*—Everett White
*Attorney, Agent, or Firm*—Jacobson, Price, Holman & Stern, PLLC

[57] ABSTRACT

Use of at least one polymer or one biopolymer, called HBGFPP, specifically protecting the growth factors of the FGF and beta TGF families from tryptic degradation in the manufacture of a drug for the treatment of muscular tissues.

14 Claims, 13 Drawing Sheets

▲ FGF
○ FGF plus heparin
● FGF plus mesoglycan
△ FGF plus sulodexide

DAYS

○ FGF$_1$
● FGF$_1$ plus heparin
▲ FGF$_1$ plus mesoglycan
△ FGF$_1$ plus sulodexide

DAYS

△ FGF2
● FGF2 plus heparin
▲ FGF2 plus mesoglycan
○ FGF2 plus sulodexide

Elution volume (m³)

DRUG AND PHARMACEUTICAL COMPOSITION FOR THE TREATMENT OF MUSCLES

FIELD OF THE INVENTION

This invention relates to the use of polymers or biopolymers for the preparation of a drug for treating lesions of all origins affecting the skeletal muscle or the cardiac muscle in human or veterinary medicine and pharmaceutical compositions for this treatment.

BACKGROUND

The synthesis of CMDBS polymers (dextrans substituted by carboxymethyl, benzylamine and sulfonate) has been described in French Patent 2461724 and U.S. Pat. No. 4,740,594. Some of these polymers mimic heparin and may be used as plasma heparin replacement products, thanks to their anticoagulant and anticomplement properties.

Some of these CMDBS polymers mimic another property of heparin consisting of a stabilization, protection and potentialization of the in vitro biological activity of the growth factors of the FGF family (Tardieu and coll., Journal of Cellular Physiology, 1992, 150, pp. 194 to 203).

French Patent 2 644.066 describes the use of certain CMDBSs associated with FGFs for healing the skin and the cornea. Experiments have been conducted by provoking a cutaneous wound with the help of a hollow punch 6 mm in diameter in the rat. In this example, the CMDBS associated with the FGF 2 makes it possible to obtain a definite effect on the speed and the quality of skin repair.

Another biopolymer, dextran sulfate, has also been advanced in association with FGFS, as a stabilizer and protector, in Japanese Patent No. 13890. Dextran sulfate, moreover, is widely used in skin healing ointments and creams as well as in collyrium compositions, but, to the knowledge of the applicant, has no reported effect on the healing and regeneration of muscular lesions.

Another agent, sucrose sulfate ester and its aluminum salt, sucralfate, are products described and used, on their own or associated with FGFs, as agents in the treatment of ulcers and lesions of the digestive tract (U.S. Pat. No. 3,432,489 and U.S. Pat. No. 5,202,311).

The skeletal and/or cardiac muscular tissues are particularly rich in growth factors and several authors have described the presence and/or action of FGFs and beta TGFs in and on myoblastic cells (e.g. D. Gospodarowicz and Cheng, In Vitro Cellular and Developmental Biology 1987 23(7): pp. 507–514; Groux-Muscatelli B., Bassaglia Y., Barritault D., Caruelle J. P. and Gautron J., Dev. Biol. 1990, 142: pp. 380–385; Johnson S. and Allen R., Exp. Cell Res. 1990, 187: pp 250–254; Dayton W. and Hathaway M., Poult Sci 1991 70: pp 1815–1822) as well as their extraction from skeletal or cardiac muscles (e.g. Morrow and coll., J. Clin. Invest. 1990, 85: pp 1816–1820; Padua R. and E. Kardami, Growth Factor 1993, 8: pp 291–306; Parker T. and Scheinder M., Annu. Rev. Physiol., 1991, 53: pp 179–200; Casscells W. and coll., Ann. N.Y. Acad. Sci. 1990, 593: pp. 148–161).

The healing action of FGFs in cardiac muscle lesions induced by ischemia creation has been described (Yanagisawa-Miwa and coll., Science 1992, 257: pp 1401–1403).

Franco (U.S. Pat. No. 4,378,347) has also described the use of an FGF, particularly in the treatment of cardiac ischemias. Dextran beads are used as excipient in certain formulations described in this patent.

The activity of the composition is very clearly attributable to the FGF.

An analysis of the prior art therefore reveals that polymers have already been used in association with growth factors.

However, none of the polymers in the documents cited above present effects on their own, that is to say without being associated with growth factors.

Moreover, the activity of polymer-factor associations has been described only on certain lesions of a particular tissue type, namely cutaneous tissue.

Due to the unpredictable nature of the therapeutic effects of a given molecule, it was not clear whether these polymers could have an effect on tissues other than those of the skin.

It is, in fact, well known that the different tissues of the human or animal body present structural and functional specific features making it impossible to predict the effect of a molecule, known for its effect on the cutaneous tissue, in the case of the muscular tissue.

This is particularly true in view of the fact that muscular tissues are very different, both in terms of their structure and origin (mesodermic), from tissues of the epiderm and the cornea.

Similarly, it is well known that it is impossible to predict the in vitro activity of a molecule on a particular tissue from results obtained in vitro on a specific experimental model.

SUMMARY OF THE INVENTION

Surprisingly, it has been found, according to the invention, that certain polymers have a very marked effect on the healing and regeneration speed of the lesions of skeletal and/or cardiac muscular tissues, and on the quality of this healing and/or regeneration, such that this speed may be measured by studying the degree of maturation of the muscular fibers, using histological and physiological methods.

This invention relates to the use of at least one polymer or one biopolymer, called HBGFPP, specifically protecting the growth factors of families of FGFs and beta TGFs from tryptic degradation and not significantly inhibiting coagulation, in the manufacture of a drug for the treatment of muscular tissues.

In particular, such a polymer presents an anticoagulant activity of less than 50 international units per mg of polymer measured, according to Maillet et al. (Mol. Immunol, 1988, 25, 915–923). Advantageously, the polymer potentializes the FGFs in vitro.

Preferably, it does not substantially activate the complement system, that is to say, it possesses an anti-complement system of above 0.5 μg for the $CH_{50}$ (according to Mauzac et al., Biomaterials, 6, 61–63, 1985).

Figure 1:
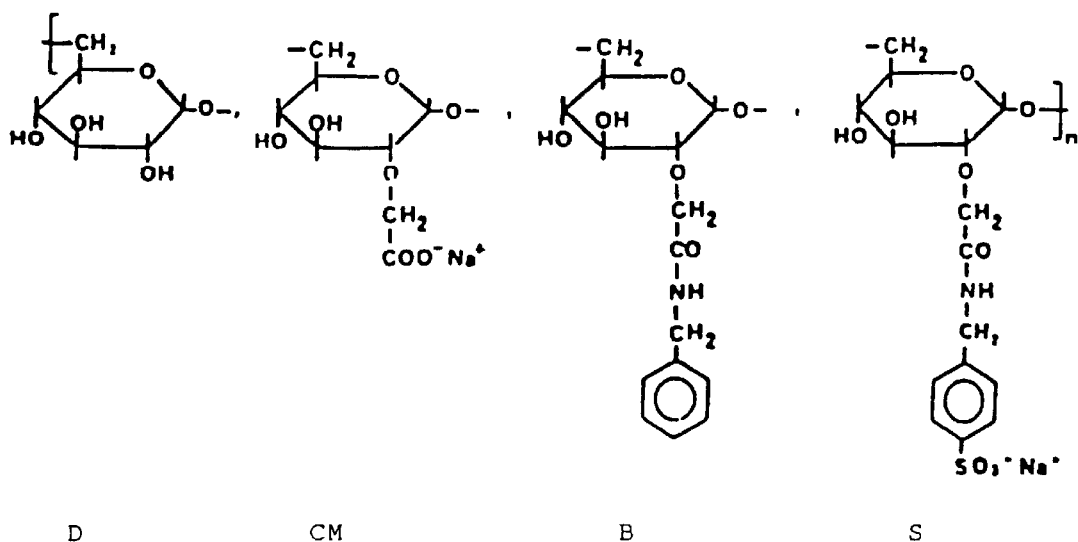
FIG. 1 represents the CMDBS formula.

According to the invention, polymers are understood to mean any natural substance, chemically modified natural substance or totally synthetic substance responding to the definition given above.

The following polymers are therefore concerned:

polymers obtained from dextrans but modified by other types of substitutions with other types of radicals, natural polymers other than those deriving from dextrans but including osidic residues (cellulose, chitin, fucans, etc.), polymers obtained by polymerization of monomers of non-osidic nature (malic polyacid, oxalic polyacid, lactic polyacid, polystyrene, polyethylene glycol), whether or not modified.

Advantageously, said polymer or biopolymer is a polysaccharide which may be principally composed of glucose residues.

Such a polysaccharide will preferably present a molecular weight above 10 kD and advantageously about 40 kD.

It may also comprise glucosamine and/or uronic acid residues, particularly in the form of glucosamine dimer-uronic acid.

Particularly preferred polysaccharides are substituted dextrans, glycosaminoglycans possibly in association with a lipid, a peptide or a protide, or sulfates of these polymers.

This invention also relates to a pharmaceutical composition containing these polymers.

The polymers and/or biopolymers may be selected from natural substances which may then be modified, if required, by additions of appropriate chemical groups, or again be obtained entirely by synthesis. These natural, semi- or wholly synthetic polymers are then selected on the basis of their ability to interact specifically with several growth factors, notably those of the FGF and beta TGF families. They are also selected on their ability to protect this (or these) factor(s) against proteolytic degradations. These polymers will be referred to under the generic abbreviation HBGFPP (heparin binding growth factor protectors and promoters).

Two prototypes of these polymers or biopolymers are given as examples together with the processes and selection criteria of these polymers.

The first HBGFPP example belongs to the CMDBS family which are known products, namely functionalized biospecific dextrans, substituted by carboxymethyl, benzylamide and benzylamine sulfonate. These polymers illustrate the yielding of HBGFPPs from natural products (dextrans) which are subsequently chemically substituted.

The second example describes the selection of wholly natural products, such as purified sulfate proteoglycosaminoglycans from tissular extracts.

These two examples illustrate the ability of these HBGFPPs to interact, stabilize, protect and potentialize the growth factors of the FGF and beta TGF families, and their use in a pharmaceutical composition permitting the healing and regeneration of skeletal muscular cells and the protection and healing of cardiac muscular cells.

In this patent application, by "treatment" is understood to mean any curative or preventive operation carried out for the prophylaxis and healing of muscular tissue lesions.

Thanks to the action of the HBGFPPs and in particular of the CMDBSs, as illustrated by the examples described below show, muscular reorganization is accelerated whereas the architecture of the muscle, that is to say the number of fibers per organized bundle in the case of the skeletal muscle, is not significantly modified. Where the cardiac muscle is concerned, the number of myocytes destroyed after the lesion brought on by ischemia is much lower than that counted after treatment by the HBGFPPS. (These results are corroborated by the decrease in the number of fibroblasts and collagenous fibers in hearts treated with HBGFPPs.) They illustrate the cytoprotective effect of the HBGFPPs.

A drug or a pharmaceutical composition according to the invention contains an efficacious quantity of HBGFPP, for example CMDBS associated with one or more compatible and pharmaceutically acceptable vehicles. It may also be associated with pharmaceutical agents such as anti-inflammatory agents or antibacterials and, for the cardiac muscle, antiarrhythmics, anticoagulants or thrombolytic agents. The vehicle may be a physiological serum or buffers such as PBS containing 0.15M NaCl or any other compatible and non irritant sort of solution for the damaged muscular tissue. Formulations providing thick or gel solutions according to standard techniques known to the person of ordinary skill in heart may be proposed depending on the type and the accessibility of the lesion.

Advantageously, such a drug is designed to be directly injectable by intramuscular route at a dose of 25 to 2500 μg/ml of HBGFPP, illustrated by CMDBS in the examples, or by HBGFPP natural polymers such as mesoglycans, but the drug may also be administered intravenously. In addition to their heparin binding growth factor protective qualities, the HBGFPPs selected according to the tests described below present a very weak anticoagulant activity compared to that of heparin, too weak to perturb coagulation in the case of a muscular trauma. In the case of an injection by intravenous route, the injected dose must be adjusted to the blood volume of the human or animal receiving treatment so that the dose of HBGFPP in the blood also lies between 25 and 2500 µg/ml.

As examples of applications of the drugs according to the invention, mention may be made of muscular, congenital or acquired atrophies and/or dystrophies, and more specifically:

genetic diseases: such as myopathies (Duchenne's, Becker's), girdle dystrophies, etc., diseases involving muscular atony, iatrogenic drug accidents (chloroquinine treatment or intramuscular local anesthetic injections), traumatic accidents such as those sustained by sportsmen and women: pulled, torn and strained muscles, hematomas etc., lesions induced by injuries or surgical acts, viral or bacterial aggressions, for example polyoma virus, muscular atrophies resulting from lack of movement, peripheral muscular ischemias such as those generated by peripheral obliterating arteriopathies of the limbs.

With regard to the cardiac muscle, the lesions generated by the reduction and elimination of blood irrigation may be prevented or diminished by the use of the composition of the invention. Thus, in the case of myocardial infarction, the injection of the composition into the infarcted muscle, or its injection by intravenous route, allows the HBGFPPs access to the damaged cardiac territory.

In the case of cardiac transplantation, as well as with cardiomyoplasties, the survival of cardiac cells may be favored by the addition of the drug or composition according to the invention.

In the case of cardiac insufficiencies generated in hereditary diseases, such as Duchene's or Becker's disease, or in myocardiopathies linked to viral, parasitic or bacterial infections.

An advantage of the invention is that the use of a single dose of the composition gives the required result, in other words the complete regeneration of the skeletal muscular fibers and the preservation of the cardiac myocytes.

Another advantage, with respect to muscular tissue lesions, is that the revacularization of the damaged muscle is also favored.

In the examples given in the following pages with reference to the skeletal muscle, a single injection of 25 µg/ml CMDBS on the site of the wound induces a complete regeneration of the muscular fibers after 7 days whereas nothing of the sort is observed in the control muscle. The number of fibers per surface unit in the histological cross section is ten times greater than in a control untreated with CMDBS.

It should be noted that neither heparin nor dextran sulfate present properties on muscular regeneration. Although these molecules interact with the FGFs, and at any rate as far as heparin with the beta TGF is concerned, neither sucrase, nor heparin nor dextran sulfate protect the beta TGF against the proteolysis induced by the action of trypsin, as is shown by the application of screening and selection tests of the HBG-FPPs described in the examples below. Thus, by carrying out in vitro screening on the basis of a double protection of the FGFs and beta TGFs against the proteolysis induced by trypsin, it is possible to select HBGFPPs, like certain CMDBSs including those given in these examples. These same selection criteria applied to natural biopolymers such as mesoglycan or sulodexide have shown that mesoglycan, which presents a double protection and stabilization activity for both FGFs and beta TGFs, has a favoring activity in muscular repair and regeneration, belongs to the HBGFPP family, whereas sulodexide, which protects FGFs against the proteolysis induced by the action of trypsin, has no significant protective action against the action of trypsin on beta TGFs.

The invention will be illustrated, but in no way limited by, the following examples:

EXAMPLE 1

CMDBS Preparation and Selection a) CMDBS preparation

CMDBSs are dextrans substituted by carboxymethyl, benzylamide and benzylamide sulfonate groups. The method of synthesizing the CMDBSs may be that described by M. Mauzac and J. Josefonvicz in Biomaterials 1984, 5, pp 301–304. According to this process, carboxymethyl dextran (CMD) is prepared from dextran by substituting several glycosylated units with carboxyl groups on the carbon in positions 5 and 6. In the next phase, benzylamide is coupled with the carboxyl groups to form carboxymethyl-benzylamide dextran (or CMBD). Lastly, a few aromatic nodes of benzylamide are sulfonated in order to yield carboxymethyl dextran benzylamide sulfonate or CMDBS.

The sodium salts of these derivatives are ultrafiltered, lyophilized and dissolved in the appropriate buffer prior to use.

The general formula of the CMDBSs is illustrated in FIG. 1.

The CMDBS possess a statistical distribution of the different substituents. The percentages for each CMDBS type are determined by using standard methods.

b) CMDBS selection i: FGFs protection and stabilization tests

During the synthesis of the CMDBS the substitution rate of each of the groups may be controlled by modifying the substitution reaction conditions. Control of such parameters as temperature, reaction time, relative concentrations of the constituents, substitution reaction number, etc., makes it possible to obtain a very large number of substituted polymers. The substitution of the hydroxyls by carboxymethyl on the carbons in positions 5 and 6 gives carboxymethylation rates ranging from 0 to 200% (100% for each of the carbons in position 5 and 6). The carboxymethyl group may, in turn, be partially or totally used for fixing the benzylamide. The benzylamide groups may be partially or totally used for the sulfonation. The functionalized substituted dextrans used according to the invention are among those specifically described in French Patent 2,461,724. In addition to its ability to stabilize and protect FGF family growth factors, as described in the publication of Tardieu et coll., J. Cell. Physio. 1992, 150, pp 194 to 203 and in French Patent 2,461,724, the selected DCMDBS must be able to interact with at least one member of the growth factors family belonging to the beta TGF family according to an evaluation method described below, and to protect the beta TGFs against proteolysis.

ii. Evaluation of the interaction capacities between CMDBSs and beta TGF family growth factors.

In order to measure the capacity of certain CMDBSs to interact with members of the beta TGF family and, by means of this interaction, to protect the beta TGFs, a grading test was devised. This test consists in measuring the ability of the selected CMDBS to allow the beta TGF to maintain its biological activity despite a protease treatment.

In the example below, the CMDBS used is batch 26.2 defined by a substitution rate of 110% of carboxymethyl units, 3.6% of benzylamide units and 36.5% of sulfonate units, and possesses an anticoagulant activity of 4 IU/mg (International Units). This batch's anticomplement activity is 1.1 μg of $CH_{50}$ measured according to Mauzac et al. (previously cited).

The heparin used as control was supplied by the Sanofi company (Choay Institute) and presents an anticoagulant activity of 175 IU/mg.

The beta 1 TFG is prepared from human blood platelets according to a protocol described in numerous publications (for example Growth factors and their receptors, 1992, vol 1 pp 419–472, written by A. Roberts and M. Sporn, edited by A. Roberts and M. Sporn, and published by Springer Verlag Berlin) and are commonly used by persons of ordinary skill in the art. The beta TGF biological activity test used in this example is that of the inhibition of CCL64 cells (from the American Tissue Culture Collection). This inhibition is measured by the ability of the beta TGF to inhibit the incorporation of tritiated thymidine in a dose dependent manner in these CCL64 cells stimulated by the FGF or by fetal calf serum according to the protocol described by Van Zolen in Progress in Growth Factor Research, 1990, 2, pp 131 to 152.

Two doses of beta TGF are used, one corresponding to the 50% inhibition capacity of the incorporation of tritiated thymidine (defined as the inhibiting activity unit) and the other corresponding to the 100% inhibition capacity. In this example, the values obtained are 250 μg of TGF for the CCL64 cells cultivated in 1 ml of culture medium.

A 50 ng sample of beta TGF in saline phosphate buffer containing 0.1% bovine albumin serum (from the SIGMA company, Saint Louis, U.S.A.) is incubated on its own, or associated either with 5000 μg of CMDBS or 5000 μg of heparin, with or without 500 μg of trypsin. The final volume of the incubated solution is adjusted to 1 ml and incubation is carried out at 37° C. for a varying length of time (10 minutes in the example described (Table 1)).

20 μl samples of are taken from each of the incubation reactions and added to CCL64 cells cultivated in 24-well plates, each well containing milliliter of culture medium according to the aforementioned protocol described by E. Zohlen. In these conditions, the final concentration of beta TGF per well is 1 ng/ml. Table 1 summarizes the results obtained in various conditions and shows the protective effect of the CMDBS. Thus, after 10 min of incubation at 37° C., 75% of the biological activity of the beta TGF is still present, whereas heparin, despite the fact that it can be fixed to the beta TGF (Mac Caffrey et al., J of Cell. Physiology, 1992, vol 52, pp 430–440), does not protect the beta TGF against this proteolytic degradation (less than 20% of biological activity remain). It should be remembered that, in the case of FGFs, heparin provides protection against proteolysis induced by trypsin (Tardieu et al., Journal of Cellular Physiology, 1992, 150: pp. 194–203).

It was verified that the CMDBS had no inhibiting power on the activity of trypsin (Table 2). Thus, 10 μg of trypsin was incubated, either with a substrate (S.87 supplied by the Serbio company in Paris and used according to the supplier's recommendations) or with this substrate and a trypsin inhibitor such as that originating from soya (such as the Soybean Trypsin Inhibitor or STI from Sigma), these incubations being carried out in the absence or presence of varying quantities of CMDBS (batch AM26). The enzymatic activity of trypsin was measured by spectrophotometric absorption of the transformation product of S 87 in versus of the incubation time.

EXAMPLE 2

Selection of Other HBGFPPs

Two commercial preparations of proteoglycosaminoglycan and glycosaminoglycans were selected according to their ability to interact with the growth factors of the FGF and beta TGF families.

Preparations of heparan sulfate obtained by fractionating mesoglycan and sulodexide were also tested.

Mesoglycan and sulodexide were provided by the SIGMA Chemical company, Saint Louis, Mo., U.S.A., as previously mentionned.

Figure 2A:
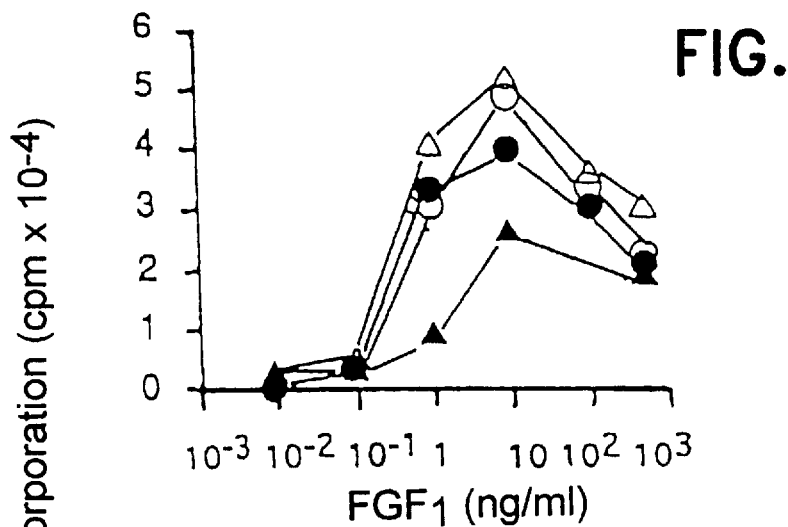
FIGS. 2A and 2B illustrate the potentialization of the biological activity of FGF1 (2A) and FGF2 (2B) by heparin, mesoglycan and sulodexide. Biological activity is measured on CCL39 cells by measuring the increased incorporation of tritiated thymidine in function of the dose of FGF1 and FGF2 added alone or in the presence of 20 μg of heparin, 10 μg of mesoglycan or 10 μg of sulodexide.
Figure 2B:
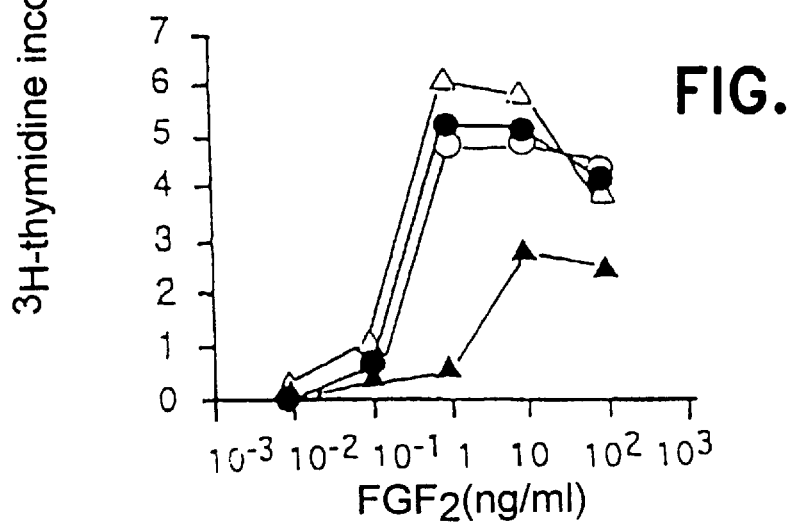
Figure 3A:
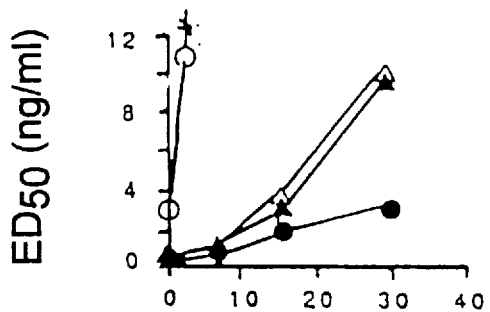
FIGS. 3A, 3B, 4A and 4B illustrate the protective effect of heparin, mesoglycan and sulodexide against a thermal degradation of FGF1(3) and FGF2(4). FGF samples are incubated on their own or in the presence of 20 μg of heparin, 10 μg of mesoglycan or 10 μg of sulodexide at 20° C. (a) and 37° C. (b) for 1, 7, 15, 30 days. The measurement of the biological activity presented in abscissa corresponds to the stimulation unit values ($ED_{50}$) of the incorporation of tritiated thymidine in CCL39 cells.
Figure 3B:
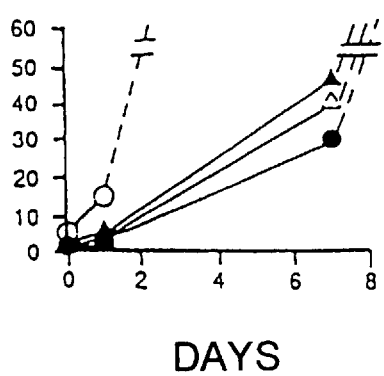
Figure 4A:
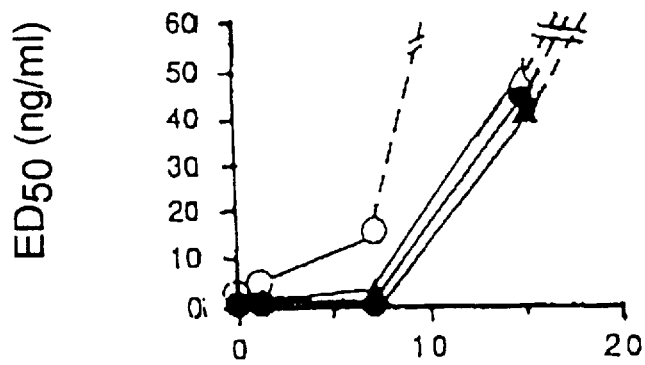
Figure 4B:
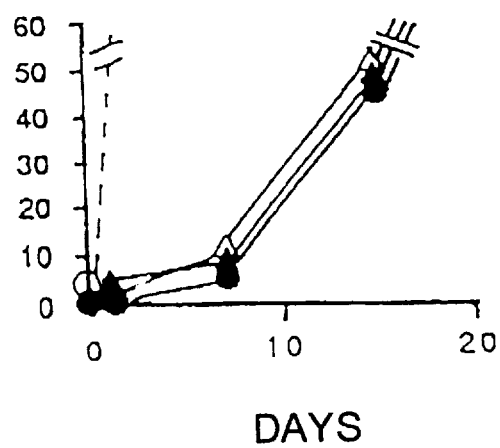
Figure 5A:
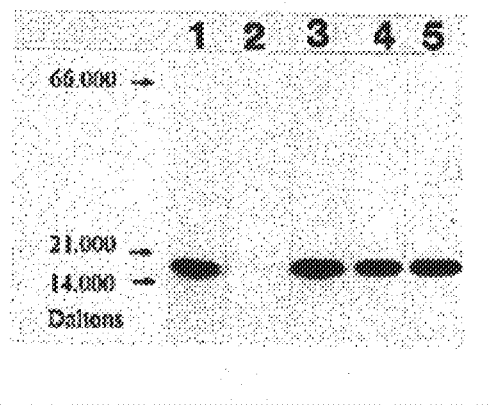
FIG. 5A illustrates the protective effect of heparin, mesoglycan and sulodexide against a proteolytic degradation of the $^{125}$I-FGF1. Proteolytic digestion was carried out at 37° C. and the samples were separated by 18% polyacrylamide gel electrophoresis. The gels are dried and autoradiographed. The first track contains the $^{125}$I-FGF1 on its own. The $^{125}$I-FGF1 is incubated in the presence of trypsin (track 2), heparin (track 3), mesoglycan (track 4) or sulodexide (track 5).
Figure 5B:
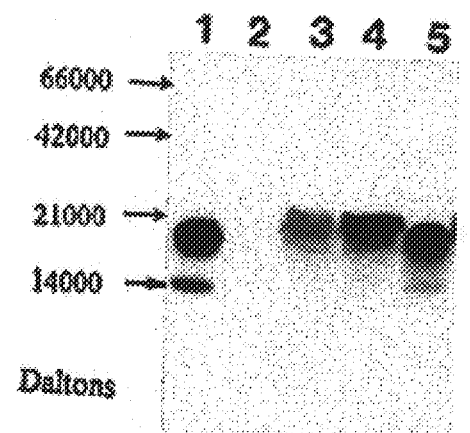
FIG. 5B illustrates the protective effect of heparin, mesoglycan and sulodexide against a proteolytic degradation of the $^{125}$I-FGF2. The arrangement of the tracks is identical to that presented for the $^{125}$I-FGF1 in FIG. 5A.

The cells used in this example are CCL39 cells from the American Tissue Culture Collection. The conditions concerning culture and the measurement test of FGF biological activity are the same as those described in the publication by Tardieu and coll. in the Journal of Cellular Physiology, 1992. Their properties are summarized in Table 3. The FGF growth factors used are the FGF 1 and FGF 2 recombinant forms.

a) Effect of mesoglycan and sulodexide on the in vitro biological activity of the FGFs In these experiments, the FGF 1 or 2 is used at a dose corresponding to the effective dose (called $ED_{50}$) in order to induce a stimulation of the biological activity of 50% of the dose inducing the maximum stimulation. The biological activity is measured by the ability to induce an increase of the incorporation of tritiated thymidine in the cells according to protocols extensively described in numerous publications such as the previously mentioned publication by Tardieu et coll. and also in French Patent 2 644 066. In this example, the $ED_{50}$ is 5 ng/ml for the FGF 1 and 3 ng/ml for the FGF 2, these values being measured experimentally (FIGS. 2A and 2B). The same stimulation experiment in function of the FGF dose is carried out in the presence of 10 μg/ml mesoglycan or sulodexide, or 20 μg/ml heparin. FIG. 2 shows that in these conditions the $ED_{50}$ becomes 0.4 ng/ml and 0.2 ng/ml respectively for the FGF 1 and FGF 2 in the presence of these doses of mesoglycan or heparin. In addition to this ability to potentialize the biological activity of the FGFs, the HBGFPPs protect the FGFs against thermal degradations and the inactivation induced by the proteolytic action of trypsin (FIGS. 3 to 5). Similarly, these HBGFPPs protect FGF1 and 2 against an inactivation induced by the proteolytic activity of trypsin (5A and 5B).

b) Protective effects of mesoglycan, sulodexide, dextran, dextran sulfate and sucrase with regard to beta TGFs.

Several other compounds were evaluated: dextran sulfate (Sigma Chemical, molecular weight 40.000), the dextran having been used for the synthesis of the CMDBS (also from Sigma)), sucrase or sucrose octasulfate (supplied by D. Bar Shalom, Bukh Medic company, Denmark). Some of these compounds were chosen because they protect and stabilize FGFs, for example sucrase (see. U.S. Pat. No. 5,202,311) or dextran sulfate (see. Japanese Patent 138 907/88). The dextran is the one used in the synthesis of CMDBS AM 26.

The protection experiment of the beta TGF biological activity was carried out in the same way as with the CMDBS and as described in Example 1 ii. The incubation mixture contained 50 ng of beta TGF (in 0.1% bovine serum albumin) and trypsin (500 μg). Mesoglycan or sulodexide or dextran sulfate or dextran or sucrase are used at the dose of 5000 μg.

The beta TGF biological activity is measured as described above after a dilution of 50 times and by using CCL64 cells.

The results are presented in Table 4.

These results show that, with the exception of certain CMDBSs capable of responding to the two selection criteria with regard to the FGFs and beta TGFs, only mesoglycan, of the other compounds tested, presents a significant protective activity for the beta TGFs.

c) Isolation of the heparan sulfate fraction of sulodexide and mesoglycan

Sulodexide and mesoglycan correspond to mixtures of several substances essentially made up of different glycosaminoglycans (GAG).

By means of a first purification stage, it was established that a gram of dry product of each of these two products contained respectively 874 mg for the mesoglycan and 795 mg for the sulodexide of total GAGs. This purification was obtained by subjecting these solubilized products to ion exchange chromatography (DEAE-Trisacryl) in order to remove all proteic contaminants. The total GAGS were then purified by eluting the DEAE gel with a sodium acetate solution, pH 4, containing 1.5M NaCl.

After an extensive dialysis phase against water, 60 mg of each product of GAG are digested by the ABC chondroitinase overnight for one night at 37° C. (1 unit per mg of GAG). This enzyme degrades all the GAGs with the exception of the heparan sulfates (HS). The digestion products were subjected to molecular sieve chromatography (G50 Sephadex, 1.8×95 cm column). Elution was then carried out on ammonium bicarbonate buffer at a rate of 18 ml/hour. The non digested material corresponding to HS-type GAGs was collected in the elution dead volume of the column.

The concentrations in GAG are calculated from their uronic acid content using the carbazol method (Bitter T. and Muir H. M., 1962, Anal. Biochem 4, pp. 330–334).

From these measurements the following composition of each of the products was obtained:

|  | Sulodexide | Mesoglycan |
|---|---|---|
| Total GAGs | 79% | 87% |
| Heparan Sulfate Fraction (HS) | 48% | 52% |
| Other GAGs | 31% | 35% |

Figures 6A, 6B:
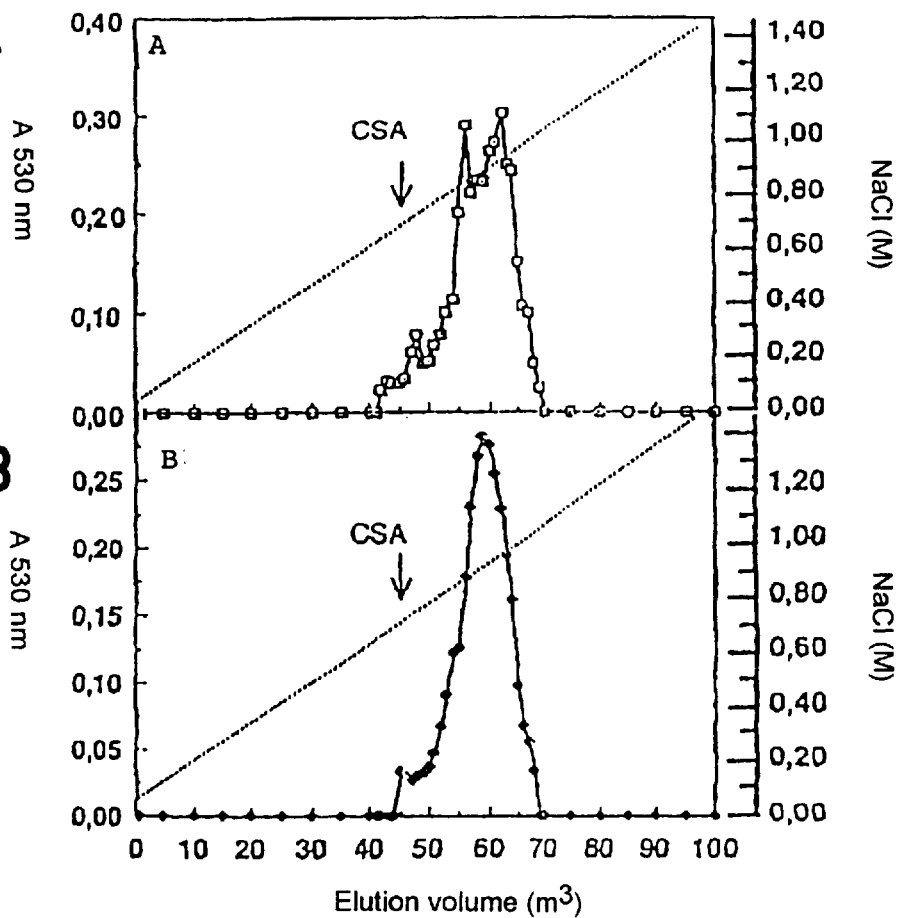
FIGS. 6A and 6B are DEAE-Trisacryl column elution profiles, respectively of HSM fractions (FIG. 6A) and HSS fractions (FIG. 6B) in the presence of chondroitin sulfate (CSA) fractions for the calibration of the column.

The HS fractions of each of these two products were again chromatographed on a DEAE Trisacryl gel. 1 mg of each HS fraction, purified with mesoglycan (FIG. 6A) or sulodexide (FIG. 6B) in 3 ml, was deposited on a balanced column with 0.05M NaCl buffer, 0.05M TMS-Hel pH 7.5. After washing of the column with 10 volumes of the same buffer followed by washing with 10 volumes of 0.05M NaCL buffer, 0.05M of sodium acetate pH 4, the material fixed to the column is desorbed by a saline gradient ranging from 0.05M NaCl to 1.5M NaCl in the same acetate buffer. 1 ml of each fraction collected was measured by the carbazole method.

The material corresponding to the HS constituents of each of the original products presents approximately the same elution profile and thus roughly the same apparent load. This elution peak maximum is obtained for a saline concentration of 0.94M NaCl. A defined fraction of chondroitine sulfate (CSA) was subjected to the same protocol in order to calibrate chromatography. This CSA fraction, containing only one sulfate group by disaccharide, is eluted at the ionic strength of 0.72M NaCl.

These results show that the HS fraction contains more sulfate groups than the reference CSAs. The HS fraction presents about two sulfate groups per dissacharidic unit.

These fractions were tested in order to discover their protective power with regard to the beta TGF and the FGF compared to the powers established with the respective raw products.

Semi-quantitative evaluation of the FGF protective effects by different polymers As described above, a constant quantity of radioactive FGF is incubated under various conditions. After autoradiography of the reaction products, the non degraded quantity of radioactive FGF is quantified by densitometry. The values correspond to the percentage of radio-labelled FGF found, compared to the quantity deposited at the start of reaction (Table 5).

The results of Tables 4 and 5 show that the HSM and HSS fractions, originating respectively from mesoglycan and sulodexide, present protective effects which are greater than these two compositions and are close to 100%.

EXAMPLE 3

In Vitro Inhibiting Effects of CMDBSs and Glycosaminoglycans on the Activity of Leukocytic Elastase and Plasmin The inhibiting powers of different CMDBS and of the intermediate compounds of their synthesis were established for leukocytic elastase and plasmin.

The purified leukocytic elastase was obtained by Elastin Products Co (Owenville, Mo., U.S.A.) and the plasmin from SIGMA.

The inhibition of enzymatic activities by these different compounds is carried out at 37° C. in a thermostatic bath. The enzymes under consideration are placed in solution in a 100 mM Tris-HCL buffer, pH 8 for the elastase and pH 7.4 for the plasmin, in the presence of 0.02% sodium azide and 0.01% Triton X100 for the plasmin. The substrate and enzyme concentrations are: 0.10 mM MeO-Suc-Ala-Ala-Pro-Val-pNA (paranitroanilide) for the elastase at 8.3 nM, and 0.20 mM dVal-Leu-dLys-pNA for the plasmin at 77 nM. The $IC_{50}$ is determined for each of the conditions.

Table 6 gives the results obtained, in which batch AM6 corresponds to a T40 dextran of 40,000 kD. Batch EM5 corresponds to a T10 dextran of 10,000 kD. The intermediate products of synthesis are identified by the symbols given above with an index number specifying the number of each substitution reaction.

The $IC_{50}$ values show that the CMDBSs have non competitive hyperbolic-type inhibiting effects on leukocytic elastase activity which are comparable to those of heparin, one of the best inhibitors of this activity (Ki of the order of 1 nM). In addition, and unlike heparin, the CMDBSs show inhibiting effects on plasmin.

Table 6 also shows that the inhibiting effects of the HSM and HSS fractions are greater than those of mesoglycan and sulodexide respectively.

EXAMPLE 4

Regeneration of Skeletal Muscles after Simple Crushing

EXPERIMENT PROTOCOL

The experiment was conducted on seven Wistar rats aged two and a half months and weighing three hundred grams.

After annesthesia by ether, the EDL muscles (muscles of hind rat paws) were removed from the forefoot and mechanically damaged by applying a constant pressure on the entire length of the muscle, using a Péan forceps. The pressure was maintained for fifteen seconds, the forceps being closed at the second notch. The homogeneity of the lesion on the whole of the muscle was controlled by following its infarction for 30 seconds. The muscle was then put back in position and the skin sutured by linen thread.

The EDL muscles received a single injection of 200 µl of 50 µ/ml CMDBS or dextran sulfate (DS) diluted in PBS without calcium or magnesium. The regeneration controls were injected with the same quantity of PBS alone. Depending on the experiments, injection took place before or after the lesion of the muscle. The 200 µl were injected in one minute and the product's diffusion was ensured by leaving the muscle for two minutes before putting it back in the forefoot. Five EDL muscles were treated by the CMDBS and two by the dextran sulfate.

The treated muscles and the controls were collected after 8 days of regeneration and then immediately frozen at $-150°$ C. in isopentane. Frozen transverse sections of 10 µm thickness were made in the median region of the muscle. The dried sections were colored by Gomori trichrome.

The morphometric analysis of the number of fibers and of their diameter was performed on micrographic montages corresponding to a transverse half-section of muscle.

RESULTS

During the collection of the muscles after 8 days of regeneration, macroscopic examination reveals a difference in aspect between the muscles treated by CMDBS and those which received an injection of PBS only. The treated muscles have a dark red aspect whereas the controls have a much lighter coloring. This difference suggests, in the former instance, a richer vascularization and a higher myoglobin content. Moreover, there is a marked increase in the diameter of the muscles treated by CMDBS (see Table 7); these muscles occupy all the forefoot and push the front tibial muscle outwards.

Figure 7:
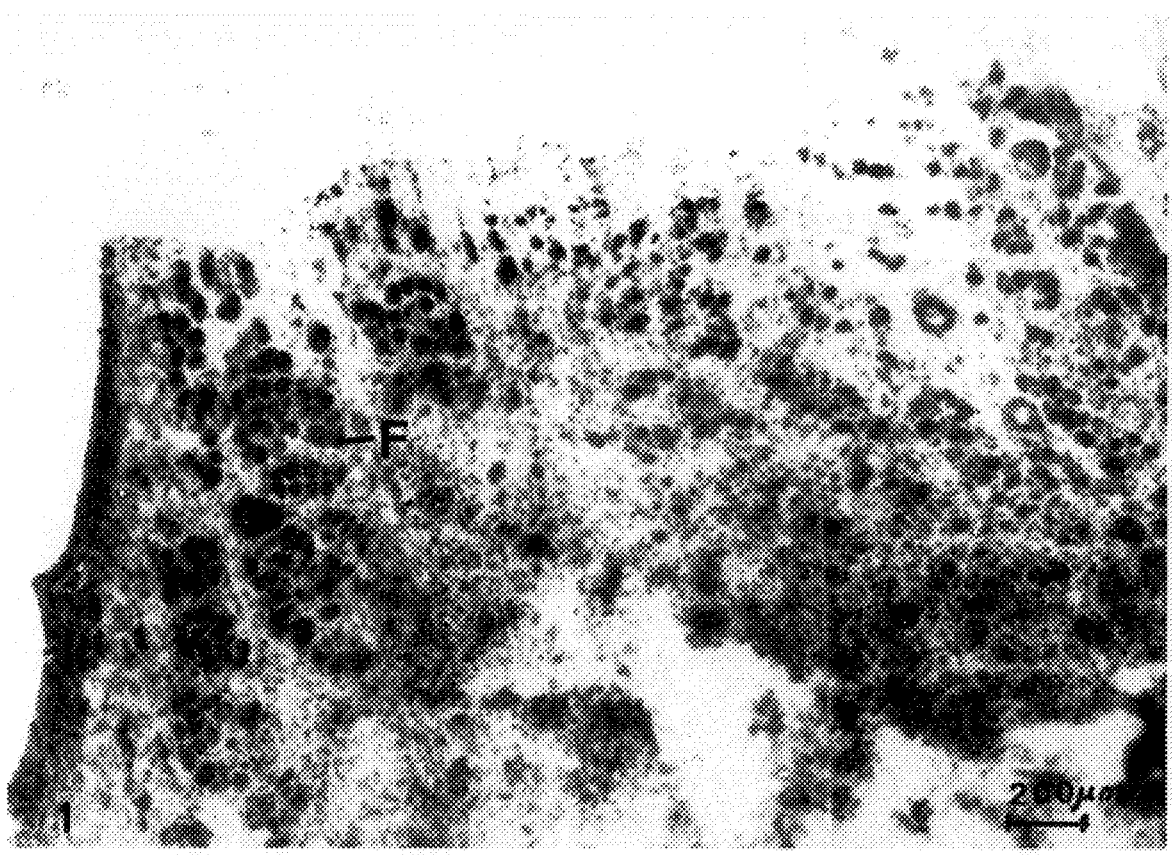
FIGS. 7, 8, 9 and 10 correspond to microphotographic montages of a muscle cross semi-section, after 8 days of regeneration, whether treated (FIGS. 8 and 10) or not (FIGS. 7 and 9) by the CMDBS.
Figure 8:
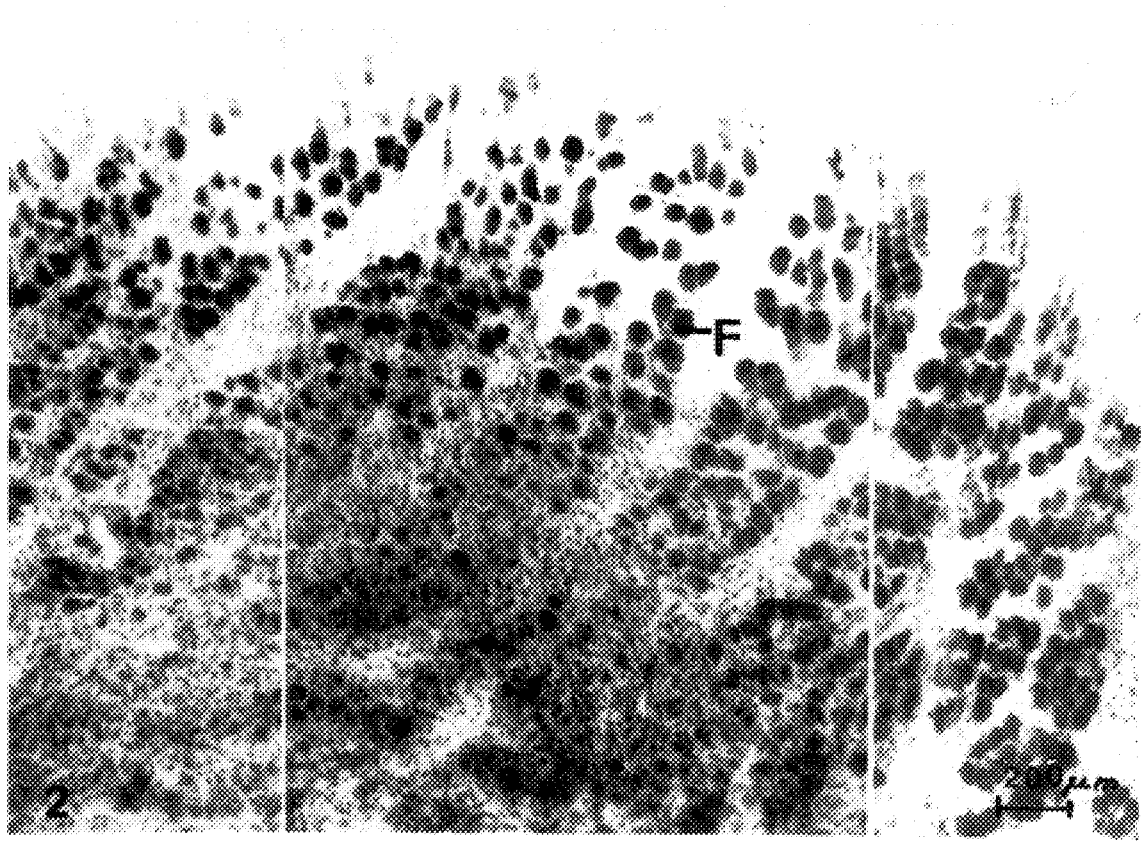
Figure 9:
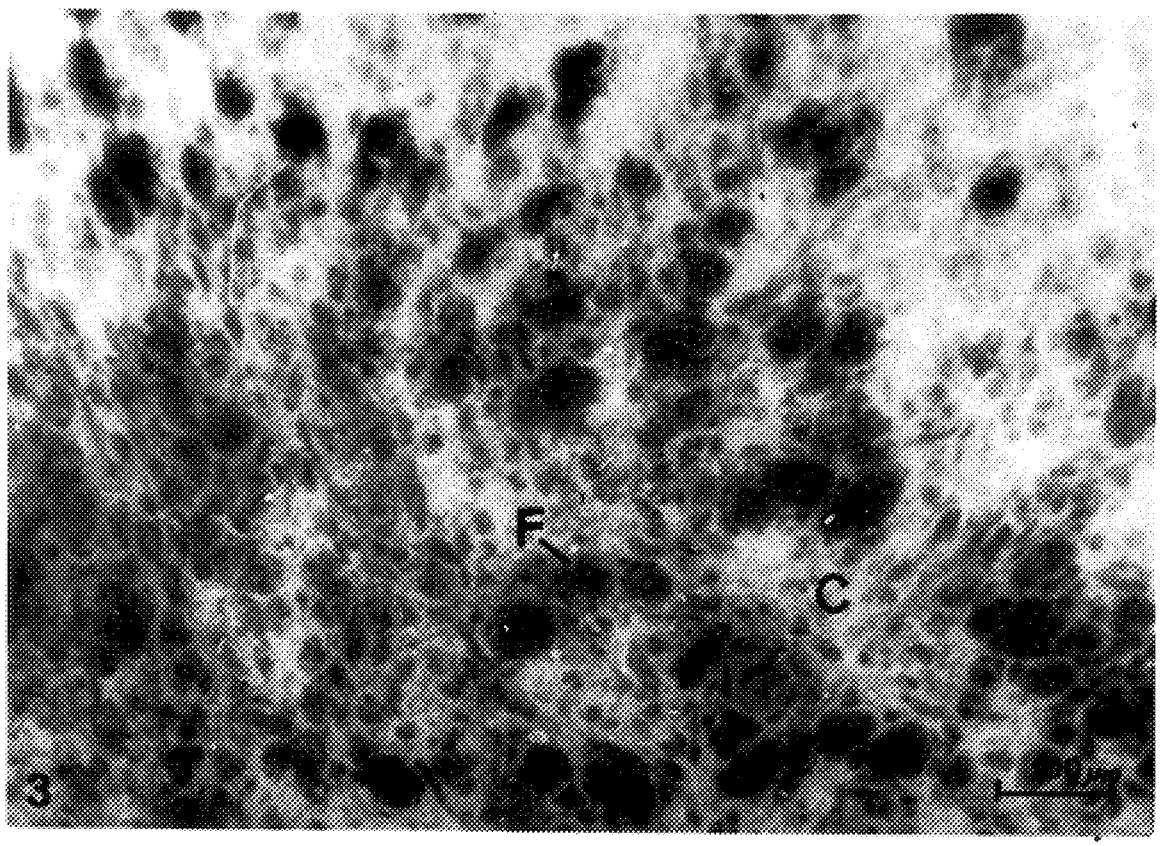
Figure 10:
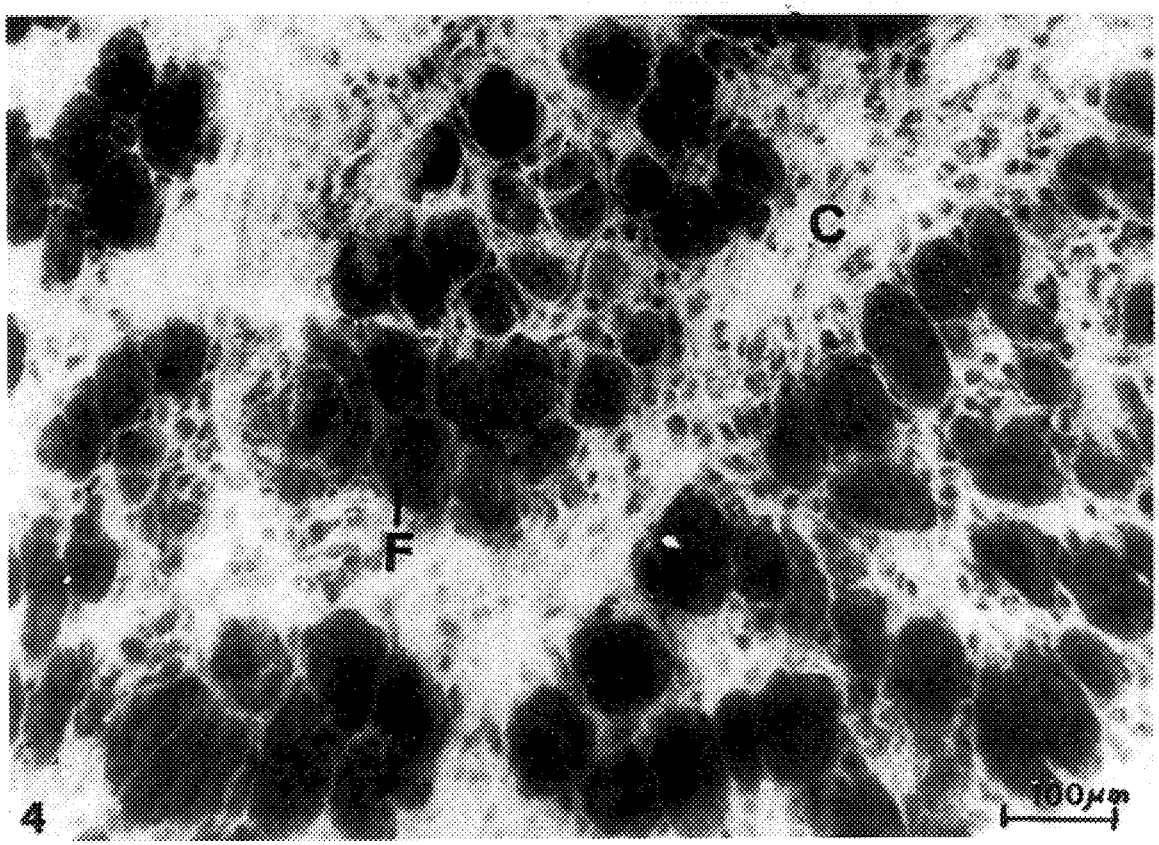
Figure 11A:
FIGS. 11A to 11D represent electrocardiograms of non operated rats (FIGS. 11A and 11B) and operated rats (FIGS. 11C and 11D).
Figure 11B:
Figure 11C:
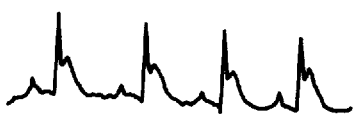
Figure 11D:

FIGS. 7 and 10 correspond to microphotographic montages of a transverse half-section of EDL muscle after 8 days of regeneration, whether or not treated by the CMDBS. The treated muscle (FIG. 8) presents a greater number of regenerated fibers (F) and has a greater diameter than the non treated muscle (FIG. 7). The single injection of CMDBS at the time of lesion also induces an improved reconstruction of the muscle: the muscular bundles, separated by the perimysium conjunctiva (C), are clearly distinguished as early as the 8th day (see FIG. 9 for non treated and FIG. 10 for CMDBS treated muscles). In normal regeneration this stage of reconstruction is not reached until after three weeks. Histological examination of the sections also shows a greater vascularization and a higher degree of reinnervation.

The results are the same, irrespective of whether the EDL muscle was injected before or after the lesion.

The data in Table 7 show that the CMDBS has a very considerable effect on the speed of regeneration (number of fibers regenerated in 8 days and on their degree of maturation (average diameter of the fibers). There is also a definite acceleration in muscular reorganization (number of bundles organized). On the other hand, the architecture of the muscle (number of fibers per bundle) is not significantly modified.

The injection of dextran sulfate, in the same conditions as for the CMDBS, results in no qualitative or quantitative modification of muscular regeneration.

EXAMPLE 5

Regeneration of a Skeletal Muscle after Deinnervation Followed by Crushing
Comparative study of different HBGFPPs and other non-HBGFPP glycosaminoglycans The experiment is conducted on 18 male Wistar rats aged two and a half months and weighing about 300 g.

The protocol is exactly the same as that described in Example 4 but the crushing of the muscle is preceded by section of the motor nerve at the entrance of the muscle.

The substances are in saline phosphate buffer solution (PBS).

Injection takes place after deinnervation and crushing , using a 50 µl microsyringe equipped with a flexible needle 60 mm in length and 0.4 mm in diameter. Two injections are carried out at an interval of 2 min. The volume injected is therefore 100 µl. The sucrase (glucose octyl sulfate) was supplied free of charge by D. Bar Shalom Bulk Medic, Denmark.

After sacrifice of the animal, the EDL muscles of the treated paw and the contralateral paw are weighed. Since individual variations in the weight of normal muscles in animals of the same age can reach 20%, the results were standardized by calculating the ratio of the treated muscle to its contralateral intact control.

This ratio was considered to be 100% for the muscles treated by PBS alone. The degree of regeneration of muscles treated by the different substances was calculated in % of the muscle injected by PBS. The results are listed in Table 8.

These results show the specific effect of HBGFPPs in muscular regeneration. In fact, only certain CMDBSs and mesoglycan, which show a protective and promoter effect for both FGFs and beta TGFs, induce a significant regeneration (190% and 133%, respectively).

EXAMPLE 6

Healing of the Cardiac Muscle

The experiments conducted during the healing of the infarcted myocardia are carried out in the rat.

The rat is a good experimental model compared to other animal species because, like in man, there is no collateral circulation between the right and left coronaries.

Experimental Protocol

Wistar rats (Wi/Wi Ico, IFFA CREDO, France), of male sex and weighing 350 g, are anesthetized with sodic pentobarbital by intra-peritoneal route.

The rats are shaved at the thorax and the neck, and a preoperative electrocardiogram (ECG) is performed.

A tracheotomy places the rat under assisted ventilation and makes it possible to combat peroperative pneumothorax and to reduce per- and postoperative mortality.

After positioning the rat in right lateral decubitus and installing a little block under the thorax, a left lateral thoracotomy is performed (at a finger's width above the floating ribs, corresponding to the 4th–5th intercostal space). The heart is exposed and the pericardia is incised, the left ventricle is identified and the left coronary artery is ligated at its origin with a PROLENE 6/0 thread. One minute later, the infarcted zone is visible, thanks to the recording of the cardiac electric activity, the Pardee waves, as an indicatory of the infarct, may be visualized.

10 µl of a 50 µg/ml solution of CMDBS prepared in physiological saline, or 10 µl of this same solution free of CMDBS, is injected right in the middle of the infarcted region, in a single point, using a Hamilton syringe.

The thorax is then closed, the pneumothorax is aspirated, and the assisted ventilation is left in place until the animal is completely awake. A final ECG is performed.

The electrocardiograms (ECG) of the rats before and after infarction at derivation are represented in FIG. 11. Traces A and B show two types of electrocardiogram which may be encountered in the non operated rats. Traces C and D show these same rats after the operation. There is a very definite over-interval of the S-T segment signing the infarct.

Rats used for this experiment will be those which, at the moment of closing the thorax, present electrical signs typical of myocardia infarction, the other animals being eliminated from the study.

After examination of the ECGs, 33 rats will be sacrificed at 7, 15 and 30 days after the operation, and an ECG performed before euthanasia. A histological study is carried out on the infarcted hearts.

The histological results are set out in FIG. 12 which shows the histological study, 15 days after the operation, of rat hearts infarcted by ligature of the left coronary artery and coloring with Masson trichrome.

Figure 12A:
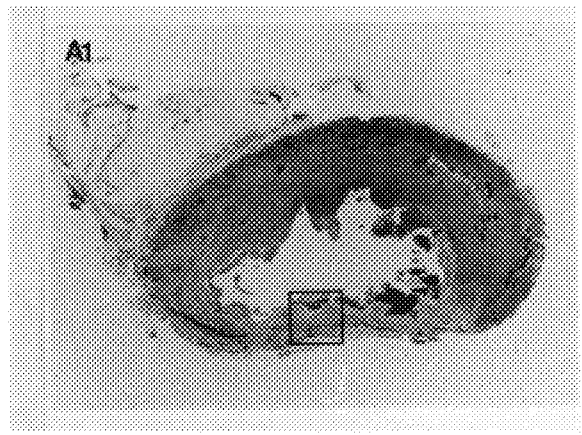
FIGS. 12A to 12F represent photographs of histological sections of the hearts of rats treated by the physiological saline (FIGS. 12A and 12D), of rats treated by CMDBS (12B and 12E) and of control rats (12C and 12F).
Figure 12B:
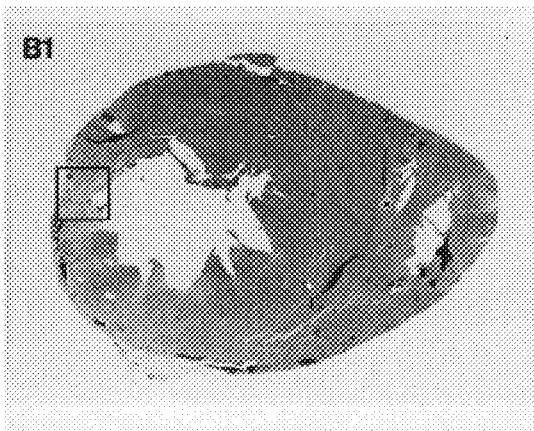
Figure 12C:
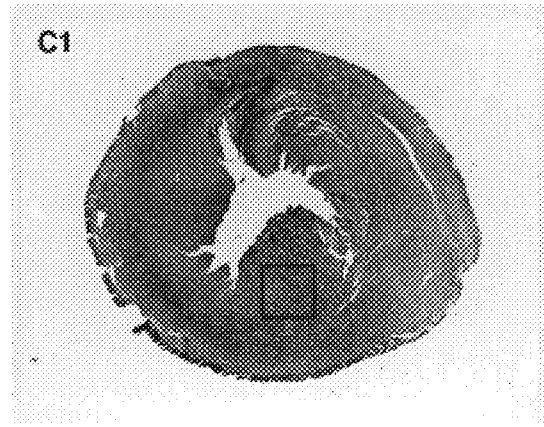
Figure 12D:
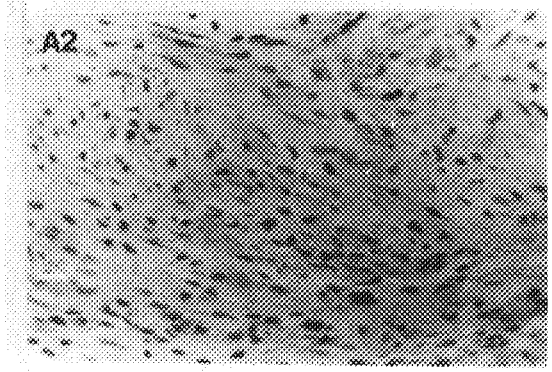

FIGS. 12A and 12D: injection of 10 μl of physiological saline in the middle of the infarcted zone. The existence is observed of a subendocardial infarction situated at the left ventricle wall (12A). This is atrophied and there is a considerable inflammatory reaction in the periphery as well as intense fibrosis. FIG. 12D (x 25) visualizes the middle of the infarction. There is substantial atrophy marked by the appearance of fibrosis and the complete disappearance of the myocardial fibers. There are some inflammatory cells.

Figure 12E:
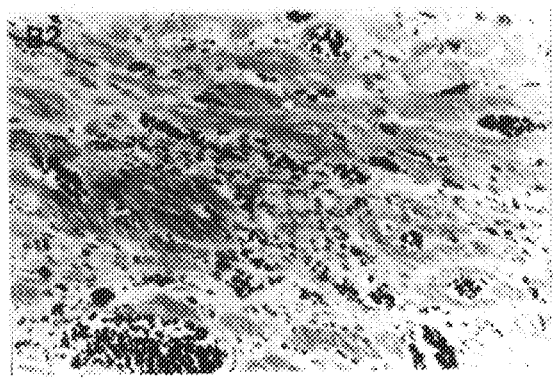

FIGS. 12B and 12E: treatment of the infarction with CMDBS (10 μl of 50 μg/ml solution are injected in the infarcted zone). Here again, there is a subendocardial infarction located at the left ventricle wall; the atrophied zone is less extended and the myocardial fibers are intact (12B=). FIG. 12E (x 25) shows numerous vascular zones and myocardial fibers apparently intact in a fibrous environment.

Figure 12F:
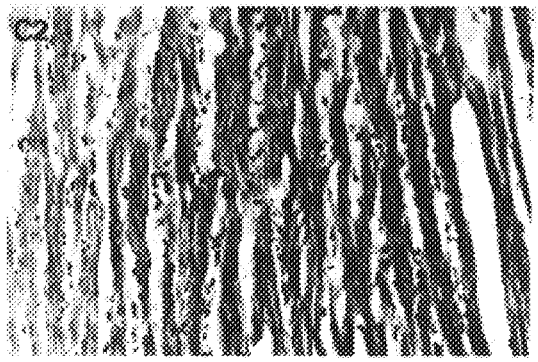

FIGS. 12C and 12F: photographs of a control heart.

It is clear that the size of the left ventricle is preserved at the wall of the hearts treated with CMDBS: the hearts in the control series present thinner walls and a wider infarcted zone. In the infarcted hearts treated with CMDBS there are myocardia regeneration zones.

TABLE 1

Protective effects of CMDBS and heparin against TGF degradation by trypsin

| incubation mixture at 37° C. for 10 min and containing, per milliliter, according to the indication: CMDBS or heparin (5000 μg): βTGF (50 ng): trypsin (500 μg) | % inhibiting activity of the incorporation of tritiated thymidine in CCL64 cells (after dilution 50 times of incubation mixture) |
|---|---|
| Incubation buffer only | 0 |
| CMDBS (5000 μg) | 0 |
| Heparin (5000 μg) | 0 |
| Trypsin (1000 μg) | 0 |
| Beta TGF (50 ng) | 100 |
| Beta TGF + CMDBS (batch AM26) | 100 |
| Beta TGF + heparin | 100 |
| Beta TGF + trypsin | 5 |
| Beta TGF + CMDBS + trypsin | 7.5 |
| Beta TGF + heparin + trypsin | 10 |

TABLE 2

Non inhibiting effect of CMDBS with regard to trypsin

| Trypsin (10 ug/ml) + S87 | 100 |
|---|---|
| Trypsin + S87 + 5 ug/ml CMDBS | 100 |
| Trypsin + S87 + 50 ug/ml CMDBS | 100 |

TABLE 2-continued

Non inhibiting effect of CMDBS with regard to trypsin

| Trypsin + S87 + 500 ug/ml CMDBS | 100 |
|---|---|
| Trypsin + S87 + STBI | 0 |

TABLE 3

Origin, anticoagulant activity and partial composition of mesoglycan and sulodexide (supplier's information)

|  | Sulodexide | Mesoglycan |
|---|---|---|
| Origin | duodenum of pig | Aorta |
| Anticoagulant activity | 50–70 IU/mg | <50 IU/mg |
| Chemical composition |  |  |
| Dermatan sulfate | 20–35% | 25–60% |
| Chondroitine sulfate | 2–7% | 3–15% |
| Heparan sulfate | + | + |

TABLE 4

Protection of the beta TGF by various polymers

| Beta TGF | 100% |
|---|---|
| Beta TGF + trypsin | 0% |
| Beta TGF + mesoglycan | 100% |
| Beta TGF + mesoglycan + trypsin | 50% |
| Beta TGF + HSM | 100% |
| Beta TGF + HSM + trypsin | 75% |
| Beta TGF + sulodexide | 100% |
| Beta TGF + sulodexide + trypsin | 20% |
| Beta TGF + HSS | 100% |
| Beta TGF + HSS + trypsin | 45% |
| Beta TGF + dextran | 100% |
| Beta TGF + dextran + trypsin | 0% |
| Beta TGF + dextran sulfate | 100% |
| Beta TGF + dextran sulfate + trypsin | 0% |
| Beta TGF + sucrase | 100% |
| Beta TGF + sucrase + trypsin | 0% |

HSM = Heparan sulfates purified from mesoglycan
HSS = Heparan sulfates purified from sulodexide

TABLE 5

Protection of the FGF by various polymers

|  | PROTECTION (in %) |
|---|---|
| FGF alone | 100% |
| FGF + trypsin | 0% |
| FGF + trypsin + heparin | 100% |
| FGF + trypsin + mesoglycan | 75% |
| FGF + trypsin + sulodexide | 70% |
| FGF + trypsin + heparinase treated mesoglycan | 0% |
| FGF + trypsin + heparinase treated sulodexide | 0% |
| FGF + trypsin + heparinase treated heparin | 0% |
| FGF + HSM + trypsin | 95% |
| FGF + HSS + trypsin | 90% |

TABLE 6

Inhibition of elastase and plasmin activities

| Compounds tested | Leukocytic elastase $IC_{50}$ in μg/ml | plasmin $IC_{50}$ in μg/ml |
|---|---|---|
| CMDBS, batch AM6 | 2.2 | 1.5 |
| T40 | >100 | >100 |
| CMDBS, batch EM5 | 10 | 7 |

TABLE 6-continued

Inhibition of elastase and plasmin activities

| Compounds tested | Leukocytic elastase $IC_{50}$ in µg/ml | plasmin $IC_{50}$ in µg/ml |
| --- | --- | --- |
| T10 CMD2B | 50 | 53 |
| T10 5CMD1B | >100 | >100 |
| T10 3CMD | >100 | >100 |
| T10 | >100 | >100 |
| Mesoglycan | 72 | 65 |
| HS mesoglycan | 20 | 22 |
| Sulodexide | 79 | 75 |
| HS sulodexide | 25 | 20 |
| Heparin | 1.8 | |
| Lipo-heparin | | 0.5 |

HSM = Heparan sulfates purified from mesoglycan
HSS = Heparan sulfates purified from sulodexide

TABLE 7

Morphometric data of EDL muscles, in cross section, treated or not by CMDBS, after 8 days of regeneration

| | Contralateral control EDL | EDL treated by CMDBS | EDL treated by dextran sulfate |
| --- | --- | --- | --- |
| Diameter of muscles in mm | 4.1 ± 0.1 | 6.2 ± 0.4 | 3.9 ± 0.4 |
| Number of fibers on a half-section | 519 | 5523 | 418 |
| Density of regenerated fibers (nb/mm$^2$) | 67.4 | 639.2 | |
| Mean diameter of regenerated fibers | 30.16 ± 2.5 | 56.4 ± 3.62 | 28.2 ± 4.6 |
| Number of muscular bundles per section | 7 | 15 | |
| Number of fibers per bundle | 67.7 ± 7 | 75 ± 14 | |

TABLE 8

Effects of different polymers on the regeneration of deinnervated muscles

| Substances: weight injected | Ratio regenerated/ contralateral intact | % ratio treated/ ratio degenerated |
| --- | --- | --- |
| PBS | 0.705 | 100 |
| CMDBS (10 µg) | 1.342 | 190 |
| Sucrase (10 µg) | 0.620 | 87 |
| Heparin (10 µg) | 0.590 | 86 |
| Sulodexide (10 µg) | 0.638 | 90.7 |
| Mesoglycan (10 µg) | 0.940 | 133 |

We claim:

1. A method for treating skeletal or cardial muscular tissue in a mammal, which comprises administering to the mammal a therapeutically effective amount of a polymer or bipolymer which is a HBGFPP (heparin binding growth factor protector and promoter).

2. A method of claim 1 wherein the polymer or biopolymer presents an anticoagulant activity of less than 50 international units per mg of polymer.

3. A method of claim 1 wherein the polymer does not substantially activate the complement system.

4. A method of claim 1 wherein the polymer potentiates the FGFs in vitro.

5. A method of claim 1 wherein the polymer substantially inhibits the proteasic activity of elastase and/or plasmin.

6. A method of claim 1 wherein the polymer or biopolymer is a polysaccharide.

7. A method of claim 6 wherein the polysaccharide is principally composed of glucose residues.

8. A method of claim 6 wherein the polysaccharide comprises a residue selected from the group consisting of a glucosamine residue and a uronic acid residue.

9. A method of claim 8 wherein the polysaccharide comprises a glucosamine-uronic acid dimer.

10. A method of claim 8 wherein the polysaccharide is a proteoglycosaminoglycan or a glycosaminoglycan, or a sulfate of one of these compounds.

11. A method of claim 6 wherein the polysaccharide is a substituted dextran.

12. A method of claim 6 wherein the polysaccharide is a dextran substituted by carboxymethyl, benzylamine and sulfonate (CMDBS).

13. A method of claim 1 wherein the polymer is of non-osidic nature.

14. A method of treating skeletal or cardiac muscular tissue, which comprises administering to a human or other animal in need of such therapy an effective amount of a pharmaceutical composition containing a) a therapeutically effective amount of at least one polymer or biopolymer, which is a HBGFPP (heparin binding growth factor protector and promoter), which specifically protects the growth factors of families of FGFs and beta TGFs from tryptic degradation and does not significantly inhibit coagulation, in association with b) at least one pharmacologically acceptable excipient.

* * * * *